US005268166A

United States Patent [19]

Barnett et al.

[11] Patent Number: 5,268,166

[45] Date of Patent: Dec. 7, 1993

[54] COSMETIC APPLICATION SYSTEM

[75] Inventors: Philip J. Barnett, Parkgate; Michael R. Lowry, Chester, both of United Kingdom

[73] Assignee: Elizabeth Arden Company, Division of Conopco, Inc., New York, N.Y.

[21] Appl. No.: 910,942

[22] Filed: Jul. 9, 1992

[30] Foreign Application Priority Data

Jul. 15, 1991 [GB] United Kingdom ................ 9115275

[51] Int. Cl.[5] .............................................. A61K 7/00

[52] U.S. Cl. ...................................... 424/047; 424/45; 424/59; 424/63; 424/401

[58] Field of Search ..................... 424/47, 63, 401, 60, 424/45, 59

[56] References Cited

U.S. PATENT DOCUMENTS

| | | | |
|---|---|---|---|
| 2,853,423 | 9/1958 | Lavia | 424/60 |
| 3,177,120 | 4/1965 | Black | 424/60 |
| 3,584,115 | 6/1971 | Gebhart | 424/45 |
| 4,145,413 | 3/1979 | Usdin | 424/63 |
| 4,293,542 | 10/1981 | Lang | 424/63 |
| 4,434,154 | 2/1984 | McShane | 424/63 |
| 4,495,169 | 1/1985 | Schmolka | 424/47 |
| 4,776,515 | 10/1988 | Michalchik | 239/3 |

FOREIGN PATENT DOCUMENTS

| | | |
|---|---|---|
| 0029301 | 5/1981 | European Pat. Off. . |
| 0031649 | 7/1981 | European Pat. Off. . |
| 0132062 | 1/1985 | European Pat. Off. . |
| 0134951 | 3/1985 | European Pat. Off. . |
| 0163390 | 12/1985 | European Pat. Off. . |
| 0171184 | 2/1986 | European Pat. Off. . |
| 0224352 | 6/1987 | European Pat. Off. . |
| 0234842 | 9/1987 | European Pat. Off. . |
| 0253539 | 1/1988 | European Pat. Off. . |
| 0243031 | 7/1989 | European Pat. Off. . |
| 0368494 | 5/1990 | European Pat. Off. . |
| 0441501 | 8/1991 | European Pat. Off. . |
| 0468735 | 1/1992 | European Pat. Off. . |
| 0468736 | 1/1992 | European Pat. Off. . |
| 108286 | 1/1899 | Fed. Rep. of Germany . |
| 730363 | 1/1943 | Fed. Rep. of Germany . |
| 735161 | 11/1932 | France . |
| 2415439 | 8/1979 | France . |
| 56-97214 | 8/1981 | Japan . |
| 0124713 | 7/1983 | Japan . |
| 8500761 | 2/1985 | PCT Int'l Appl. . |
| WO90/00446 | 1/1990 | PCT Int'l Appl. . |
| WO90/03224 | 4/1990 | PCT Int'l Appl. . |
| 1393333 | 5/1975 | United Kingdom . |
| 1569707 | 6/1980 | United Kingdom . |
| 2061769 | 5/1981 | United Kingdom . |
| 2073052 | 10/1981 | United Kingdom . |
| 2092025 | 8/1982 | United Kingdom . |

*Primary Examiner*—Thurman K. Page
*Assistant Examiner*—D. Gabrielle Phelan
*Attorney, Agent, or Firm*—Milton L. Honig

[57] ABSTRACT

A novel system for depositing color cosmetic materials directly onto the skin or other parts of the body utilizes the principle of electrostatic spraying to deliver the color cosmetic composition to the intended site, e.g. the skin of the face, eyelids, eyelashes, nails, etc. The system is applicable to a wide range of known color cosmetic materials.

6 Claims, No Drawings

COSMETIC APPLICATION SYSTEM

FIELD OF THE INVENTION

This invention relates to a system for depositing cosmetic agents, particularly colour cosmetic materials, onto the skin or other body parts. More particularly, the invention relates to methods and apparatus for applying such materials directly onto the skin, especially that of the face (or other parts thereof), as well as to other parts of the body such as the nails.

BACKGROUND OF THE INVENTION

Conventional systems for beautifying or otherwise treating various parts of the face, fingernails and toenails and other parts of the body, particularly the skin, rely on applying liquid, liquid based or solid, e.g. powder, products via regimes such as brushing or wiping, or alternatively direct application of the product which is in the form of a stick or pencil. These known systems are frequently location dependent, for example are restricted to use in the bedroom or bathroom, are messy, difficult to control, inconvenient and time consuming. As a particular example of this, the conventional application using a soft brush of solid powder colour cosmetic products such as blushers is particularly time consuming and it is difficult to achieve a particular desired level of colour application especially in regions where even colour fading is required.

Frequently, conventional colour cosmetic products utilise an oily carrier or vehicle base to enable the colour cosmetic to be applied at concentrations suitable for attainment of the desired cosmetic effect. Such oily carriers and other adjuncts contribute to the messiness of known application regimes and may be particularly troublesome to the user where make up for example is to be applied in various stages. These known systems also represent uneconomical use of cosmetic raw materials.

A further problem encountered with known colour cosmetic application techniques is that when such products are to be applied in multiple layers, such as when making up the face, the use of brushes, pads and other direct contact delivery means such as sticks or pencils, may often disrupt previously applied materials, so that considerable care, time and application control must be exercised if the desired cosmetic result is to be successfully achieved.

Such direct contact deposition means also suffer from the difficulty of achieving 100% coverage of any particular region of skin surface, owing to its uneven texture and surface profile, which results in inefficient use of colour cosmetic products and less than optimum attainment of desired colour cosmetic effects.

In a very different technical field, the principle of electrostatic spraying of liquid and solid materials is also known. In this technique a formulation to be sprayed is raised to a high electric potential in a spray nozzle to cause the formulation to atomise as a spray of electrically charged droplets. Such electrically charged droplets seek the closest earthed object to discharge their electric charge, and this can be arranged to be the desired spray target. Hitherto, electrostatic spraying techniques have been proposed principally for only large-scale industrial and agricultural applications, especially for delivering reactive materials like paints, adhesives and other surface coatings, as well as large-scale delivery of pesticides and other agricultural or agrochemical formulations. Examples of disclosures in this field include GB-A-1393333, GB-A-1569707, GB-A-2092025, EP-A-029301, EP-A-253539 and WO-A-85/00761, the contents of which disclosures are incorporated herein by reference. In the context particularly of electrostatic spraying of paints and other pigments, there may also be mentioned the following prior art references, the disclosures of which are also incorporated herein by reference: EP-A-234841, EP-A-195546, GB-A-1478853, GB-A-1464370, GB-A-1461385 and GB-A-1364244.

More recently, there have been a small number of proposals for utilising the known principle of electrostatic spraying for delivering particular materials in specific applications other than those mentioned above.

EP-A-224352 suggests the use of an electrostatic sprayer for delivering a pharmaceutically active agent to the eye, to replace conventional ocular treatment using eye drops.

JP-A-56-97214 (dating from 1981) suggests the use of electrostatic spraying for applying a granular (i.e. solid particles of) colouring material to hair to effect surface coating thereof. However, the disclosed system is unsuitable for small scale personal use and fails to present significant consumer applicability and appeal.

One tentative proposal for applying the principle of electrostatic delivery to the deposition of fingernail colouring materials is disclosed in FR-A-2415439, which dates from January 1978. The author of that reference suggests electrostatic projection as a means of depositing small coloured synthetic fibres to fingernails which have been pretreated with an adhesive varnish. However, this early reference contains no suggestion of how the fibres may actually be delivered to the desired target and moreover the disclosed system has little practical usefulness or consumer applicability and appeal.

SUMMARY OF THE INVENTION

As a result of identifying and appreciating the above problems, prejudices and limitations of the known art and through much experimentation, we have now devised a system which enables the principle of electrostatic spraying to be put to effective use in delivering colour cosmetic materials, such that apparatus and methods are now provided for such deposition regimes which are technically efficient, cost effective, safe, have widespread consumer applicability and appeal, and which solve or at least ameliorate many, if not all, of the problems associated with the prior art.

Accordingly, in a first aspect the present invention provides a method of depositing a colour cosmetic composition onto the skin or other part of the body, comprising electrostatically spraying the colour cosmetic composition thereon.

In more detail, the method of this aspect of the invention preferably comprises:

(a) providing an apparatus which includes:
- (i) a reservoir containing the colour cosmetic composition to be deposited which is in electrostatically sprayable form;
- (ii) at least one delivery means in communication with the reservoir;
- (iii) a high voltage generator powered from an electricity source; and
- (iv) control means for selectively applying the high voltage from the generator to the or each delivery means; and (b) actuating the said control means to electrostatically spray the colour cosmetic composition from the or each delivery means onto the skin or other part of the body.

In a second aspect, the present invention provides an apparatus for depositing a colour cosmetic composition onto the skin or other part of the body, comprising:

(a) a reservoir for containing the colour cosmetic composition which is in an electrostatically sprayable form;
(b) at least one delivery means in communication with the reservoir;
(c) a high voltage generator powered from an electricity source;
(d) control means for selectively applying the high voltage from the generator to the or each delivery means to electrostatically spray the colour cosmetic composition from the or each delivery means.

In a third aspect, the present invention provides, in combination, the apparatus as defined above and an electrostatically sprayable composition consisting of or containing a colour cosmetic material to be deposited onto the skin or other part of the body.

Having thus defined the main aspects of the present invention, preferred embodiments and various features and optional characteristics thereof will now be described in detail.

DETAILED DESCRIPTION OF PREFERRED EMBODIMENTS

Colour cosmetic materials which may be deposited using the system of the present invention can be any of a very wide range of materials. They may be used either singly or in combination and with respect to the latter it is within the scope of the invention to deliver more than one colour cosmetic material at the same time or sequentially, for example from the same or different delivery means of the apparatus. This may be particularly useful where highly controlled colour variations or particularly accurate colour control is required. Conventional colour cosmetic products often include one or more adjunct ingredients, especially oils, which assist delivery and controllability of delivery of the colour material and which are not directly associated with the particular cosmetic benefit which it is desired to achieve. A particular advantage of the present invention is that it allows at least some of, or even substantially all of, such auxiliary components to be omitted from a conventional colour cosmetic composition comprising the "active" material to be deposited. Any such auxiliary components may however still be used within the scope of this invention if desired or as necessary.

Generally there is the essential overall requirement of colour cosmetic compositions useful in the present invention that they be electrostatically sprayable.

A principal characteristic of such electrostatically sprayable compositions which it will usually be necessary to carefully select or adjust as necessary (as discussed further below), is their resistivity. Preferred resistivities fall within the range from about $10^4$ to about $10^{12}$ ohm cm, more preferably from about $10^6$ to about $10^{10}$ ohm cm. Resistivities of lower than $10^4$ may possibly be used. Resistivities of more than about $10^{12}$, e.g. up to about $10^{14}$ or more, may also be used, though such values are difficult to measure using cheap, conventional resistance measuring apparatus. Resistivity is measured using standard, conventional apparatus and methods, generally at 25° C.

Compositions to be deposited using the present invention are preferably liquids, though solid compositions may also be delivered in accordance with the invention. If the colour cosmetic material is itself liquid at room temperature, then it may be suitable for delivery on its own. Alternatively, it may be combined with one or more adjunct materials which are preferably also liquid at room temperature, though may optionally be solids if used in minor amounts and do not deprive the composition of being electrostatically sprayable. For colour cosmetic materials which are normally solid or highly viscous at room temperature, at least one solvent or carrier may be combined with it, with or without any other adjunct materials which are acceptable.

Examples of particularly preferred colour cosmetic materials which may be deposited using the apparatus and methods of the present invention include the following:

1. cosmetic foundation materials, e.g. creams or other compositions;
2. cosmetic mask formulas;
3. skin colour cosmetics e.g. blushers;
4. eye cosmetics such as eyeshadows;
5. artificial tanning materials, e.g. compositions containing dihydroxyacetone (DHA);
6. fun make-up materials.

Further possible examples of suitable colour cosmetic materials for use in the invention include:

7 lip colouring materials and varnishes;
8. coloured polymers and waxes;
9. eye cosmetics such as eyeliners, mascaras and the like;
10. nail colours, polishes, varnishes, hardeners, protectors, etc.

Specific examples of materials of the above categories are many and varied, and well known in the art.

In addition to the colour cosmetic materials mentioned above, compositions to be deposited using the present invention may also include one or more other "active" components which have a secondary cosmetic or pharmaceutical effect at their intended target site. These include for example spot treatment agents, such as ethyl lactate and benzoyl peroxide, lip protective materials such as lip salves, skin blemish treatment agents, skin whiteners, and agents for treating pigmentation disorders e.g. freckles. Such materials may advantageously be used in combination with a colour cosmetic agent to provide a deposition system having two-fold utility and extending the advantages of the principal deposition technique to the deposition of such auxiliary cosmetic or pharmaceutical actives.

Where the colour cosmetic material to be deposited is to be combined with a solvent or carrier, this is preferably an oily material, in which case the cosmetic agent is preferably soluble or solubilisable in or miscible with the solvent or carrier.

Examples of suitable solvents, diluents or carriers include the following: silicone oils, oleic acid, hydrocarbons, isopropyl myristate, oleyl alcohol, oleates, squalene, sunflower seed oil, rapeseed oil, other plant-derived oils, mineral oil, alcohols or polyols such as ethanol, isopropylalcohol, propylene glycol, dipropylene glycol, phenyl ethyl alcohol, glycerol, 1,3-butanediol, 1,2-propanediol, isoprene glycol.

If a solvent, diluent or carrier is used, it is preferably a material which does not interact chemically or physically with the surface (either untreated or pretreated with another cosmetic agent) onto which the colour cosmetic composition is to be sprayed. Where a surface is to be sprayed which has been pretreated with another cosmetic material, therefore, it is preferred that the colour cosmetic composition does not dissolve or otherwise interact with the pretreated surface layer. Preferably, any solvent, diluent or carrier which is used is volatile, so as to improve deposition and retention of the colour cosmetic material on the target surface.

Preferably, the colour cosmetic composition to be sprayed wets the target surface, either untreated or pretreated with another cosmetic material, and for this purpose one or more conventional surfactants may be included in the composition to be sprayed. Suitable surfactant may be selected from anionic, cationic, amphoteric, zwitterionic and nonionic surfactants, classes and examples of which are well known in the cosmetic art.

Preferably colour cosmetic compositions for deposition using the present invention are non-aqueous or may contain only a small amount of water, e.g. less than 10% by weight, preferably less than 5% wt, even more preferably less than 1% wt. This is because, due to its low resistivity, a predominantly aqueous composition is generally difficult to spray effectively using electrostatic means.

As mentioned above, depending upon the cosmetic composition or material to be deposited, it may be necessary to adjust its resistivity by addition of one or more resistivity adjusting materials, examples and suitable amounts of which will be either known to persons skilled in the art, or readily derivable by simple experiment. Examples of suitable resistivity adjusting agents are charged species such as salts, e.g. sodium chloride, or a salt conventionally used in buffers in personal products or pharmacological formulations. Polar substances such as alcohols, e.g. ethanol, may alternatively be used to lower resistivity, whereas non-polar substances, e.g. oils and other hydrophobic materials, may be used to increase resistivity.

In addition to resistivity, another parameter of the compositions to be sprayed which it may be necessary to carefully select and adjust is viscosity.

Materials of a wide range of viscosities may be suitable for use in the present invention, but suitably the viscosity is in the range of from about 0.1 to about 50000 mPas, more preferably from about 0.1 to about 10000 mPas, even more preferably from about 0.5 to about 5000 mPas (at 25° C). If desired or as necessary one or more viscosity adjusting agents may be included. Examples of such agents include salts, e.g. alkali metal or ammonium halides, polymers and conventional thickening materials, and oils and polar oil thickeners such as cosmetic oils, waxes, glycerides and suitable amphiphiles with melting points of for example >20° C.

Viscosity may in fact be used as a parameter to control the rate of delivery of the colour cosmetic to the intended site, if, as has been found with some embodiments of the system of the invention, it has a substantially inverse proportionality relationship with the flow rate of the material from the delivery means. For example, a particular delivery regime or a habit or need of a user may dictate an optimum delivery rate of the particular material being applied, in which case careful selection of the viscosity of the composition to be sprayed can provide a self-regulating deposition mechanism.

For use in the present invention, the hardware and electrical componentry and circuitry may be of any suitable construction and design. The art of electrostatic spraying contains many examples of suitable apparatus which may be used in the present invention and such disclosures of such apparatus or particular features thereof may be applied either singly or in combination to the spray systems of the present invention.

Examples of suitable electrostatic spraying hardware include, in addition to those of the prior art references mentioned above, those of the following published references: GB-A-2061769, GB-A-2073052, EP-A-031649, EP-A-132062, EP-A-163390, EP-A-171184, EP-A-234842, EP-A-243031, EP-A-368494, EP-A-441501, EP-A-468735 and EP-A-468736; the disclosures of all of which are incorporated herein by reference.

As will be appreciated by persons skilled in the art, particular constructional features and design and electrical and other operating parameters of such apparatuses may be selected or adjusted as necessary, in the context of the present invention, in accordance with the desired functioning characteristics, as for example dictated by the composition or material to be sprayed and/or the needs or wishes of a user.

Features of the apparatus of the present invention which may be so selected and/or adjusted include for example: voltage generated by the high voltage generator and power source, electric field strength in or in the region of the product delivery means, flow rate of the product to be sprayed from the reservoir to and out of the delivery means, size and configuration of the delivery means itself and construction and properties of any product feed mechanism utilised between the reservoir and the output of the delivery means.

In preferred embodiments of the invention, preferred voltages generated by the high voltage generator from the power source are in the range of from about 2 to about 20 kilovolts, more preferably from about 2 to about 10 kilovolts. The most suitable voltage for a given system may depend upon the product to be sprayed, as well as other parameters, all of which will generally be selected to give an overall optimised system.

Electric field strengths which are responsible for the spraying action of the electrostatic apparatus will be largely dependent upon the voltage applied. However, field strengths may be controlled or adjusted if necessary, for example by changes in nozzle configuration or geometry and/or the use of field intensifying electrodes, which are well known in the art cited above.

Optimum flow rates of material to be sprayed will often depend upon the composition of the product itself, e.g. upon the concentration of the "active" colour cosmetic ingredient(s) being applied. Also, as already mentioned with respect to viscosity of the sprayable material, a suitable flow rate may be selected depending upon the particular delivery regime and/or habit or needs of a user. By way of example, preferred flow rates of compositions for delivery in accordance with embodiments of the invention are in the range of from about 0.00001 to about 0.01 ml/sec, more preferably from about 0.0001 to about 0.001 ml/sec, per delivery means. For certain colour cosmetic materials, e.g. artificial tanning agents and other such materials conventionally applied in relatively large amounts for colouring purposes, preferred flow rates may be greater than those indicated above, for example up to about 0.05 ml/sec, or even up to about 0.1 ml/sec.

The size and configuration of the one or more delivery means in the apparatus of the invention may be of any suitable form and again may be selected in association with other parameters to give an optimised functioning electrostatic spray delivery system. Commonly the or each delivery means will be in the form of a nozzle, preferably of insulating or semi-insulating material such as plastics or various polymers, as is well known in the art.

The delivery means may advantageously include metering means to provide a dosing mechanism for delivering a predetermined fixed amount of material from the or each nozzle. Such an expedient may for example be useful in conjunction with a system having a controlled flow rate.

In preferred embodiments of the apparatus of the invention, the or each delivery means is in communication, i.e. preferably fluid communication, with the reservoir or reservoirs (if for example more than one colour cosmetic material or composition is to be desired to be sprayed from the same apparatus or even the same delivery means) by virtue of product feed means. As is well described in the prior art, such feed means may comprise a wick, e.g. a porous wick, through and/or over which the product to be sprayed flows before reaching the point of high electric field strength where it is dispersed as a charged spray of droplets or particles. Alternatively the feed means may comprise a hollow conduit through which the composition passes under the effect of capillary action. As a further alternative, in systems which for example require a particularly high flow rate, special feed means may be provided, for example a pump. This may be of any suitable type, e.g. electrically operated, but more conveniently it may be a simple mechanical device which exerts pressure on the reservoir containing the composition to be sprayed, such that the composition therein is forced out of the reservoir to the delivery means.

As is well known in the art, the apparatus according to the invention preferably include a trigger (i.e. a manual control means) or alternatively an automatic control means to selectively apply the high voltage from the generator to the or each delivery means to electrostatically spray the colour cosmetic composition agent onto the intended target, i.e. the skin or other part of the body. Any other suitable control means however, e.g. which automatically control actuation of the system, may be used, as will be appreciated by persons skilled in the art.

We claim:

1. A method of depositing a color cosmetic composition comprising the artificial tanning material dihydroxyacetone directed onto the skin, comprising electrostatically spraying the composition directly thereon, the method further comprising:

(a) providing an apparatus which includes:

(i) a reservoir containing the color cosmetic composition to be delivered which is in an electrostatically sprayable form;

(ii) at least one delivery means which is a nozzle in communication with the reservoir;

(iii) a high voltage generator generating voltage in the range 2 to 20 kilovolts powered from an electricity source; and (iv) control means for selectively applying the high voltage from the generator to the at least one delivery means; and (b) actuating the said control means to electrostatically spray the color cosmetic composition from the at least one delivery means directly onto the skin at an intended site.

2. A method according to claim 1, wherein the color cosmetic composition is a liquid.

3. A method according to claim 1, wherein the color cosmetic composition is a solid.

4. A method according to claim 1, wherein the color cosmetic composition further comprises a carrier for delivering said artificial tanning material to the skin.

5. A method according to claim 1, wherein the color cosmetic composition is deposited at a rate of from 0.00001 to 0.1 ml/sec.

6. A method according to claim 1, wherein the voltage generated by the high voltage generator is in the range of from 2 to 10 kilovolts.

* * * * *

US005268166C1

(12) EX PARTE REEXAMINATION CERTIFICATE (8293rd)
United States Patent
(10) Number: US 5,268,166 C1
(45) Certificate Issued: Jun. 7, 2011

Barnett et al.

(54) COSMETIC APPLICATION SYSTEM

(75) Inventors: Philip J. Barnett, Parkgate (GB); Michael R. Lowry, Chester (GB)

(73) Assignee: FD Management, Inc., Wilmington, DE (US)

Reexamination Request:
No. 90/010,073, Dec. 7, 2007

Reexamination Certificate for:
Patent No.: 5,268,166
Issued: Dec. 7, 1993
Appl. No.: 07/910,942
Filed: Jul. 9, 1992

(51) Int. Cl.

| | |
|---|---|
| ***A61K 8/00*** | (2006.01) |
| ***A61K 8/02*** | (2006.01) |
| ***A61Q 1/00*** | (2006.01) |
| ***A61Q 1/04*** | (2006.01) |
| ***A61Q 1/10*** | (2006.01) |
| ***A61Q 1/12*** | (2006.01) |
| ***A61Q 3/02*** | (2006.01) |
| ***A61Q 19/00*** | (2006.01) |
| ***A61Q 90/00*** | (2006.01) |
| ***A45D 29/00*** | (2006.01) |
| ***A45D 34/04*** | (2006.01) |
| ***B05D 1/04*** | (2006.01) |

(52) U.S. Cl. .............................. 424/47; 424/45; 424/59; 424/63; 424/401

(58) Field of Classification Search ........................ None
See application file for complete search history.

(56) References Cited

U.S. PATENT DOCUMENTS

| | | | |
|---|---|---|---|
| 2,949,403 | A | 8/1960 | Andreadis et al. |
| 4,508,706 | A | 4/1985 | Pawelek et al. |
| 5,121,884 | A | 6/1992 | Noakes |
| 5,268,166 | A | 12/1993 | Barnett et al. |
| 5,662,890 | A | 9/1997 | Punto et al. |

FOREIGN PATENT DOCUMENTS

| | | | |
|---|---|---|---|
| EP | 0 031 649 | | 7/1981 |
| EP | A-224352 | * | 6/1987 |
| JP | 56-097214 | | 8/1981 |

OTHER PUBLICATIONS

Lena HoglundMSc.. Assessment of DHA in Self–Tanning Creams Applied in Spray Booths. (2006).

* cited by examiner

*Primary Examiner*—Dwayne C Jones

(57) ABSTRACT

A novel system for depositing color cosmetic materials directly onto the skin or other parts of the body utilizes the principle of electrostatic spraying to deliver the color cosmetic composition to the intended site, e.g. the skin of the face, eyelids, eyelashes, nails, etc. The system is applicable to a wide range of known color cosmetic materials.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-6 are cancelled.

* * * * *